United States Patent [19]
Wagner et al.

[11] Patent Number: 5,704,945
[45] Date of Patent: Jan. 6, 1998

[54] BRAKE-ACTION KNEE JOINT

[75] Inventors: Helmut Wagner; Manfred Krukenberg, both of Duderstadt, Germany

[73] Assignee: Otto Bock Orthopaedische Industrie Besitzund Verwaltungs-Kommanditgesellschaft, Duderstadt, Germany

[21] Appl. No.: 604,744

[22] Filed: Feb. 23, 1996

[30] Foreign Application Priority Data

Feb. 24, 1995 [DE] Germany ............ 195 06 426.7

[51] Int. Cl.$^6$ ............................................. A61F 2/64
[52] U.S. Cl. ............................ 623/44; 623/46; 188/306
[58] Field of Search ........................ 623/39, 43–46, 623/36, 37, 40–42; 188/296, 309, 308, 306; 403/31, 39, 119, 120; 602/26, 16

[56] References Cited

U.S. PATENT DOCUMENTS

| | | | |
|---|---|---|---|
| 1,051,288 | 1/1913 | Szydlowski | 188/309 |
| 2,519,226 | 8/1950 | Coe | 623/44 |
| 2,530,286 | 1/1948 | Catranis . | |
| 2,568,053 | 10/1948 | Catranis . | |
| 2,667,644 | 2/1954 | Johnson . | |
| 3,015,825 | 1/1962 | Blatchford . | |
| 4,206,519 | 6/1980 | Blatchford . | |
| 4,958,705 | 9/1990 | Horvath | 188/314 |
| 5,181,931 | 1/1993 | van de Veen | 623/40 |

FOREIGN PATENT DOCUMENTS

| | | |
|---|---|---|
| 0 325 347 | 7/1989 | European Pat. Off. . |
| 0 439 028 | 7/1991 | European Pat. Off. . |
| 0576672 | 1/1994 | European Pat. Off. ......... 188/296 |
| 0 654 254 | 5/1995 | European Pat. Off. . |
| 762695 | 4/1954 | United Kingdom . |
| 1247851 | 9/1971 | United Kingdom . |

*Primary Examiner*—David H. Willse
*Attorney, Agent, or Firm*—Foley & Lardner

[57] ABSTRACT

A brake-action knee joint for a leg prosthesis includes a closed displacer chamber which concentrically surrounds the joint pin over its circumference, at least partially, is preferably filled with hydraulic oil, and is arranged in the associated end of the central part of the joint. The joint pin is designed as a rotary piston and is connected in torsionally rigid fashion to the upper part of the joint. The joint pin divides the closed displacer chamber into an extension chamber and a flexion chamber, which are connected to one another by way of an oil line which can be completely or partially closed by a valve plunger. The valve plunger is mounted in the central part of the joint in such a way as to be displaceable counter to the action of a valve-plunger spring pushing it into its open position and, when the central part of the joint is pivoted in the direction of flexion about the rocker pin arranged in the lower part of the joint, is pushed into its closed position by an adjusting device provided in the lower part of the joint.

16 Claims, 7 Drawing Sheets

BRAKE-ACTION KNEE JOINT

BACKGROUND OF THE INVENTION

The invention relates to a brake-action knee joint, the joint having an upper part, a lower part, a joint pin which is connected in torsionally rigid fashion to one part of the joint, and a rocker which forms a central part of the joint and which, with its extension-side end, is fixed to a rocker pin lying parallel, ventrally and distally with respect to the joint pin and, with its flexion-side end, surrounds the joint pin, and having a braking device activated by foot loading.

Figure 6:
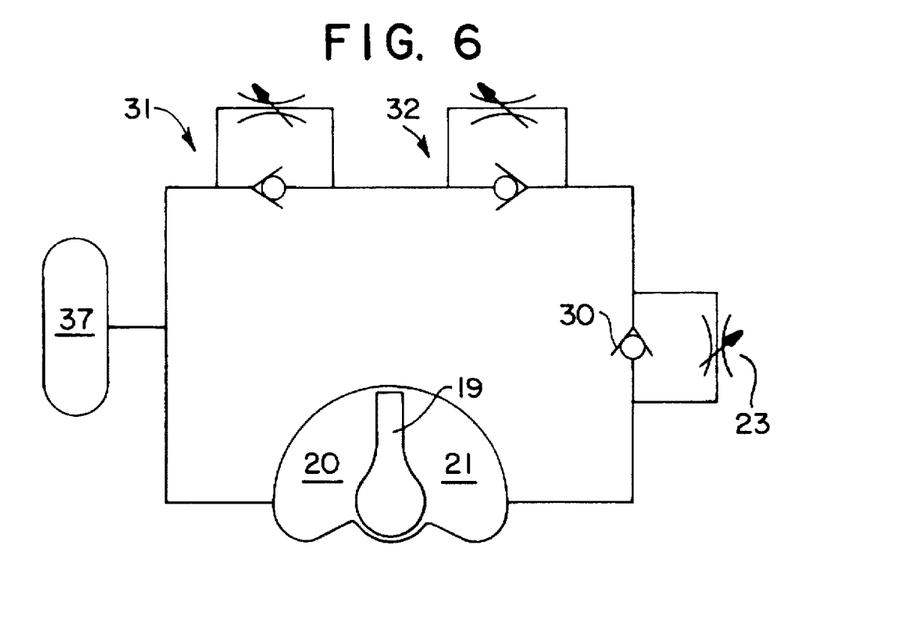
FIG. 6 shows a hydraulic flow diagram.
Figure 7:
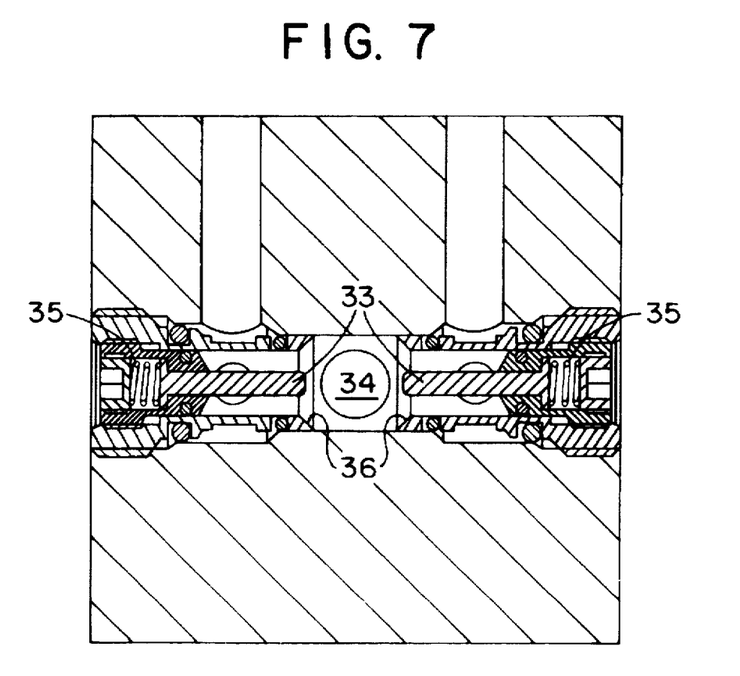
FIG. 7 shows a schematic detail illustration of the adjustable check valves for controlling the swing phase of the brake-action knee joint.

A brake-action knee joint is disclosed, for example, in U.S. Pat. No. 3,015,825. The loading-dependent automatic actuation of mechanisms for generating motional resistances to secure prosthetic knee joints against bending under load requires technical measures which allow motion of the upper and lower joint components of the leg prosthesis relative to one another, specifically in a direction which is assisted by real loading states of the leg prosthesis during the standing phase of walking. In the prior-art brake-action knee joint, the technical solution for this relative motion is the rocker which forms the central part of the joint. In this prior-art design, the rocker pin is connected to the upper part of the joint, while the joint pin is arranged in the lower part of the joint. The longitudinal axis of the rocker runs forwards and downwards, i.e. in an antero-distal direction, relative to the longitudinal axis of the extended leg prosthesis, starting from the center of the knee pivot. This inclination has the effect that the braking action exerted on the knee joint by a brake band stretched around a brake drum by the loading-dependent motion of the femoral and tibial part of the leg prosthesis relative to one another decreases continuously from its maximum at heel contact at the beginning of the supporting phase of walking to the point where the leg is supported on the forefoot at the end of said phase, since, during this process, the longitudinal axis of the rocker approaches to an ever-increasing extent a parallel position relative to the main direction of loading, as a result of which the extent of the relative motion is restricted. This circumstance, which is illustrated in FIGS. 6 and 7 of the prior publication, serves to improve the transition from the supporting phase to the swing phase of walking since it allows the amputee to initiate the bending of the knee at a point in time at which the forefoot of the leg prosthesis is still under low loading.

SUMMARY OF THE INVENTION

The object on which the invention is based is to improve the design of the brake-action knee joint described at the outset while retaining a natural walking phase for the braking device activated by foot loading.

According to the invention, this object is achieved by a closed displacer chamber which concentrically surrounds the joint pin over its circumference, at least partially, is preferably filled with hydraulic oil, is arranged in the associated end of the central part of the joint and is divided by the joint pin, which is designed as a rotary piston and is connected in torsionally rigid fashion to the upper part of the joint, into an extension chamber and a flexion chamber, which are connected to one another by way of an oil line which can be completely or partially closed by a valve plunger which is mounted in the central part of the joint in such a way as to be displaceable counter to the action of a valve-plunger spring pushing it into its open position and, when the central part of the joint is pivoted in the direction of flexion about the rocker pin arranged in the lower part of the joint, is pushed into its closed position by an adjusting device provided in the lower part of the joint.

It is advantageous here if two oppositely acting restrictor-type check valves are arranged in series in the oil line connecting the extension chamber to the flexion chamber in order to control the swing phase.

It is furthermore advantageous to provide a connecting rod which acts as an advancer, one end of which is pivoted to the upper part of the joint and the distal end of which is pivoted to a spring clamp which is accommodated in the lower part of the joint and is acted upon by an advancer spring.

In order to avoid a hard impact in the case of extension, end-position damping can be provided according to the invention. It is advantageous if, to generate end-position damping upon extension, the oil line which connects the extension chamber to the flexion chamber is connected in such a way, via a connection, to the extension chamber that the rotary piston closes this connection to an increasing extent in the last part of its rotary motion in the direction of extension. This last part of the rotary motion can preferably amount to 10°–15°. As extension progresses, the rotary piston forces the oil out of the extension chamber into the flexion chamber via a connecting line. The increasing closure of this oil outlet line by the rotary piston brings about a restriction effect which effects damping of extension. The progress of damping can be determined by means of the external shape of the rotary piston moved past the connection.

In order to avoid flow resistance caused by the end-position restrictor in the case of a reversal of the direction of rotation of the rotary piston from extension to flexion (bending), provision can be made, according to the invention, for a check valve which is opened upon introduction of the bend by the oil displaced from the flexion chamber to be provided in the connection of the oil line to the flexion chamber.

Further features of the invention are disclosed below and are explained in greater detail in conjunction with further advantages of the invention by means of exemplary embodiments.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred exemplary embodiments of the invention, and, together with the general description given above and the detailed description of the preferred embodiments given below, serve to explain the principles of the invention.

DETAILED DESCRIPTION OF THE PREFERRED EMBODIMENTS

Figure 1:
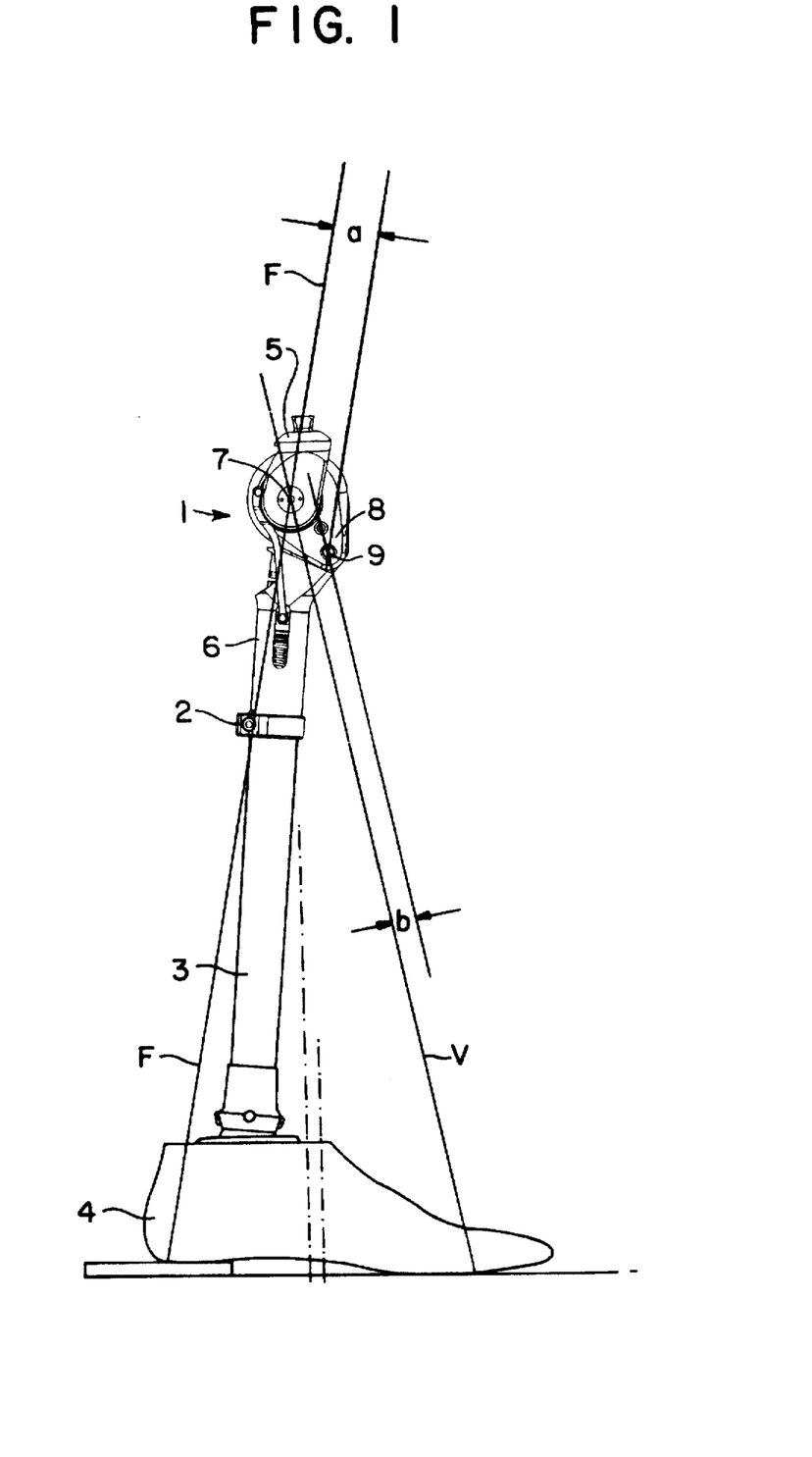
FIG. 1 shows a knee joint with a below-knee prosthesis in side view.
Figure 2:
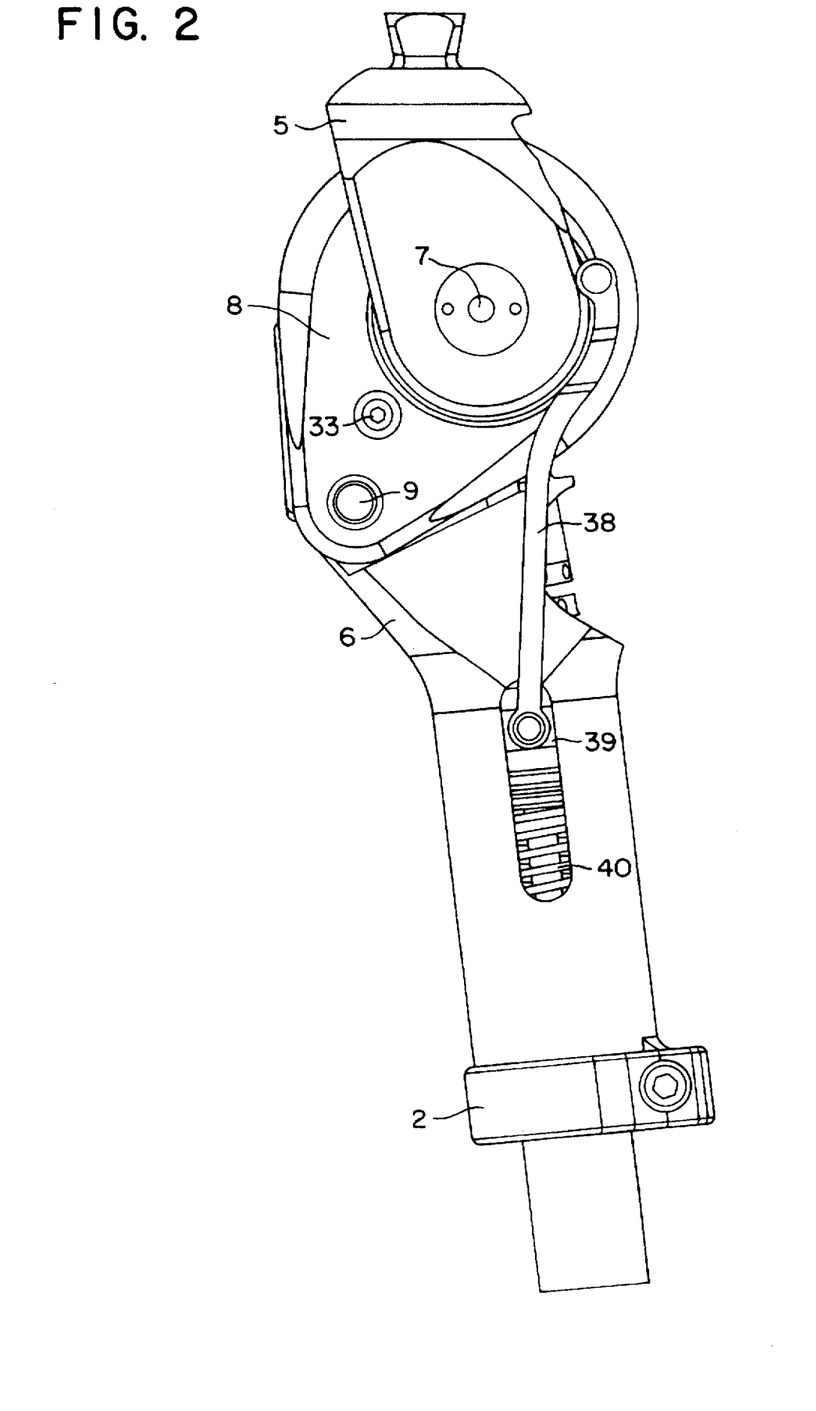
FIG. 2 shows, in side view, a brake-action knee joint with hydraulic activation system, in the position of extension.
Figure 3:
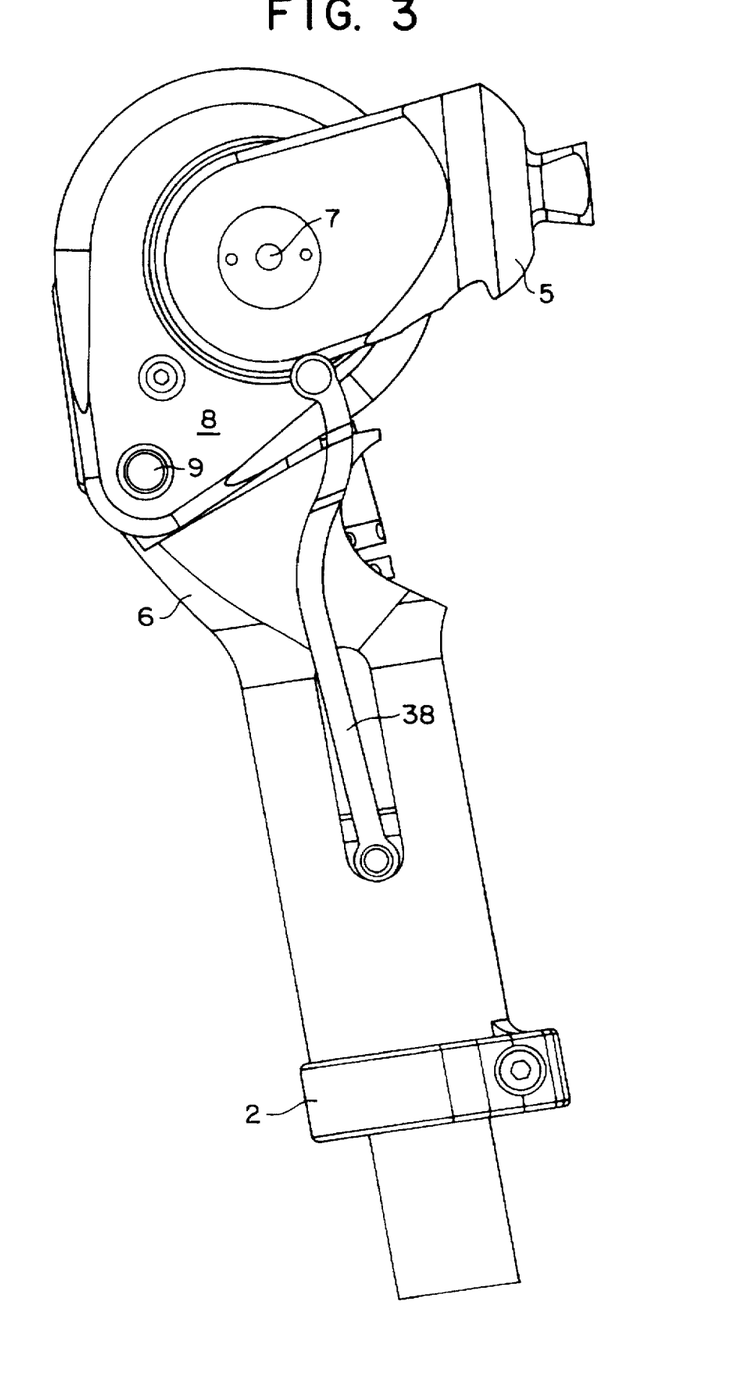
FIG. 3 shows the brake-action knee joint of FIG. 2 in the position of flexion.
Figure 4:
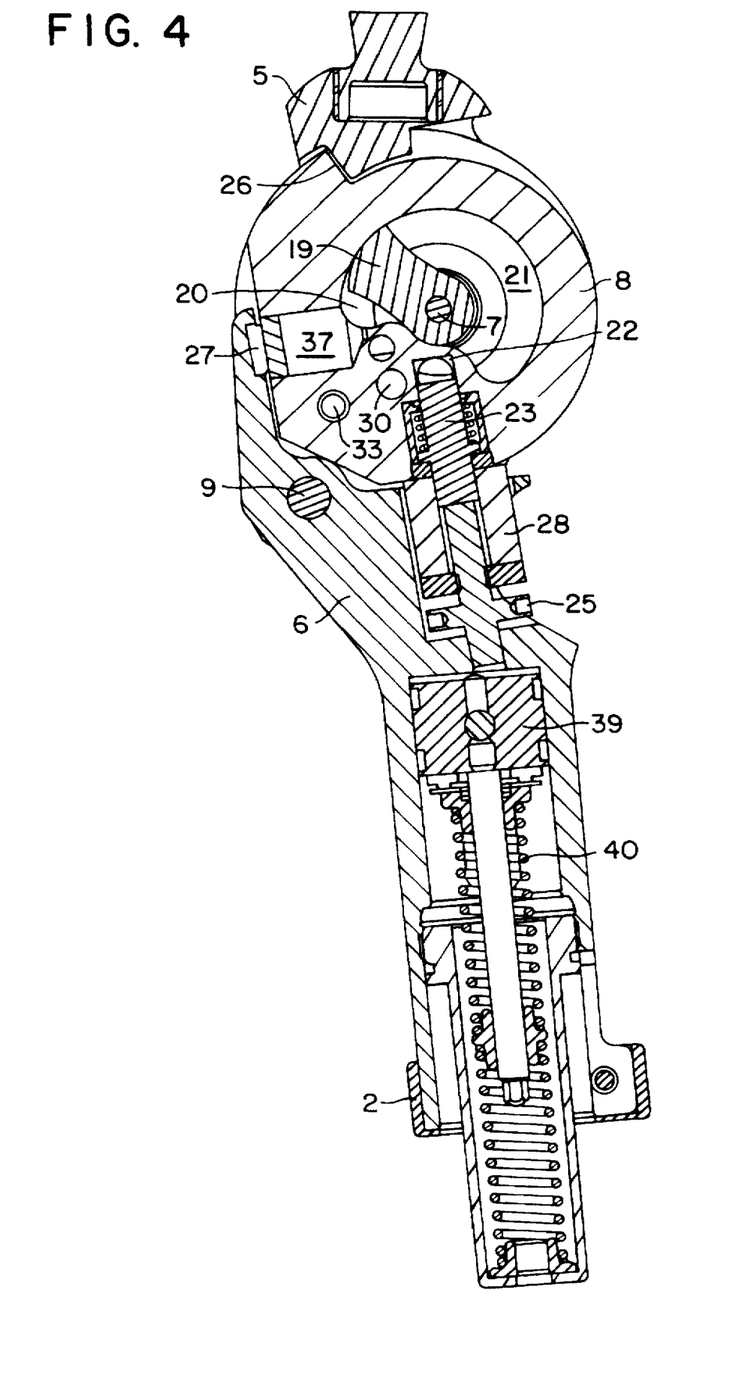
FIG. 4 shows the illustration of FIG. 2 in longitudinal section.
Figure 5:
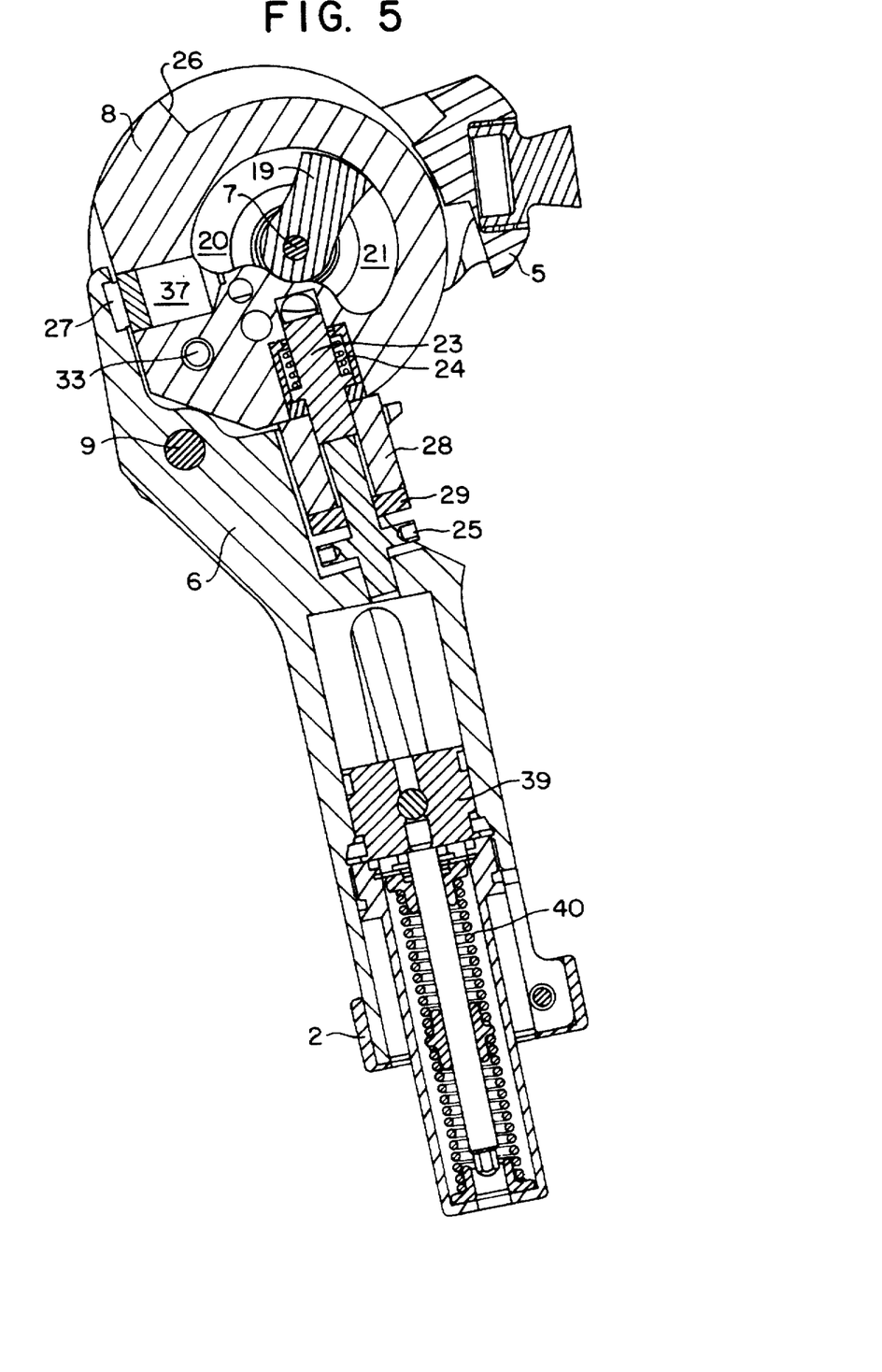
FIG. 5 shows the illustration of FIG. 3 in longitudinal section.

FIG. 1 shows a brake-action knee joint 1, attached to the distal end of which, by way of a clamp-type connection 2, is a tube 3 which forms the tibia of the prosthesis and is connected at its lower end to a prosthetic foot 4.

The brake-action knee joint 1 is made up of an upper part 5, a lower part 6, a joint pin 7, and a rocker which can be acted upon by pedal loading, forms a central joint part 8 of the joint, and can be pivoted about a rocker pin 9 lying parallel to the joint pin 7.

From FIG. 1, it can be seen that the rocker pin 9 is arranged ventrally and distally relative to the joint pin 7.

FIG. 1 shows a force line F which symbolizes the heel loading and a line of force V which symbolizes the forefoot loading, both of these lines passing through the joint pin 7. The braking torque which the rocker 8 that can be pivoted about the rocker pin 9 can exert on the joint pin 7 is determined by the respective lever arm, which depends on the distance of the respective line of loading from the rocker pin 9. From FIG. 1, it can be seen that the lever arm a of the line of heel loading F is greater than the lever arm b of the line of forefoot loading V. This is a result of the fact that the rocker pin 9 is positioned below the joint pin 7 and has the effect that, in the case of heel loading, a maximum braking torque is produced, while this braking torque is considerably lower in the case of forefoot loading and, as a result, allows the corresponding introduction of a bend for the walking phase. If the two pins 7, 9 were situated in the same horizontal plane, the heel and forefoot loading would produce approximately equal braking torques, thereby impairing the introduction of a bend for the walking phase.

FIGS. 2 to 5 show a hydraulically activated brake-action knee joint. Here, the joint pin 7 is concentrically surrounded, at least in part, at its circumference by a displacer chamber which is preferably filled with hydraulic oil, is arranged in the rocker 8 forming a central part of the joint, and is divided by the joint pin 7, which is designed as a rotary piston 19 and is connected in torsionally rigid fashion to the upper part 5 of the joint, into an extension chamber 20 and a flexion chamber 21, which are connected to one another by way of an oil line 22. The latter can be completely or partially closed by a valve plunger 23 which is mounted in the central part 8 of the joint in such a way as to be displaceable counter to the action of a valve-plunger spring 24 pushing it into its open position and, when the central part 8 of the joint is pivoted in the direction of flexion, is pushed into its closed position by an adjusting device provided in the lower part 6 of the joint. This adjusting device comprises a manually rotatable adjusting screw 25 which is mounted in the lower part 6 of the joint and acts upon the distal end of the valve plunger 23.

An extension stop 26 for the upper part 5 of the joint is provided on the central part 8 of the joint. The rotary motion of the central part 8 of the joint mounted on the rocker pin 9 into its position of extension is limited by an extension stop 27 seated on the lower part 6 of the joint and its rotary motion into its position of flexion is limited by a resilient flexion stop 28 likewise fixed to the lower joint part 6 and formed by a rubber sleeve which partially surrounds the valve plunger 23 and the adjusting screw 25 of the latter. This resilient flexion stop 28 is used for the changeover from the swing phase to the supporting phase and can be adjusted to a preload matched to the patient by means of an adjusting nut 29 which acts upon the distal end of the rubber sleeve and is guided on the adjusting screw 25.

A check valve 30 which bypasses the restriction formed by the valve plunger 23 and opens upon extension of the joint and the resulting oil flow from the extension chamber into the flexion chamber is provided in the oil line 22 which connects the two chambers 20, 21 to one another (see also FIG. 6). This prevents the hydraulic oil displaced during the extension of the joint from being affected by the valve plunger 23.

In order to be able to control the swing phase, two oppositely acting restrictor-type check valves 31, 32 are arranged in series in the abovementioned oil line 22 (see FIGS. 6 and 7) and these check valves can each be acted upon by means of a respective adjusting pin 33 that can be longitudinally adjusted from outside manually. FIG. 7 shows that the two check valves 31, 32 have a common ball 34, which can be displaced between the two adjusting pins 33 given the imposition of sufficient pressure. The balls 34 are subjected to pressure by the oil flow around them. As the oil flow increases, the pressure acting on the ball 34 increases, the ball 34 thereby being moved closer to the corresponding valve seat 36 counter to the action of a spring 35. This results in greater restriction of the oil flow. The resistance (damping) thus increases in the case of a relatively rapid knee movement.

An accumulator 37 which compensates for changes in volume of the hydraulic oil is connected to the displacer chamber 20, 21.

A connecting rod 38 which acts as an advancer, one end of which is pivoted to the upper part 5 of the joint and the distal end of which is pivoted to a spring clamp 39 which is accommodated in the lower part 6 of the joint and is acted upon by an advancer spring 40 is furthermore provided.

Figure 8:
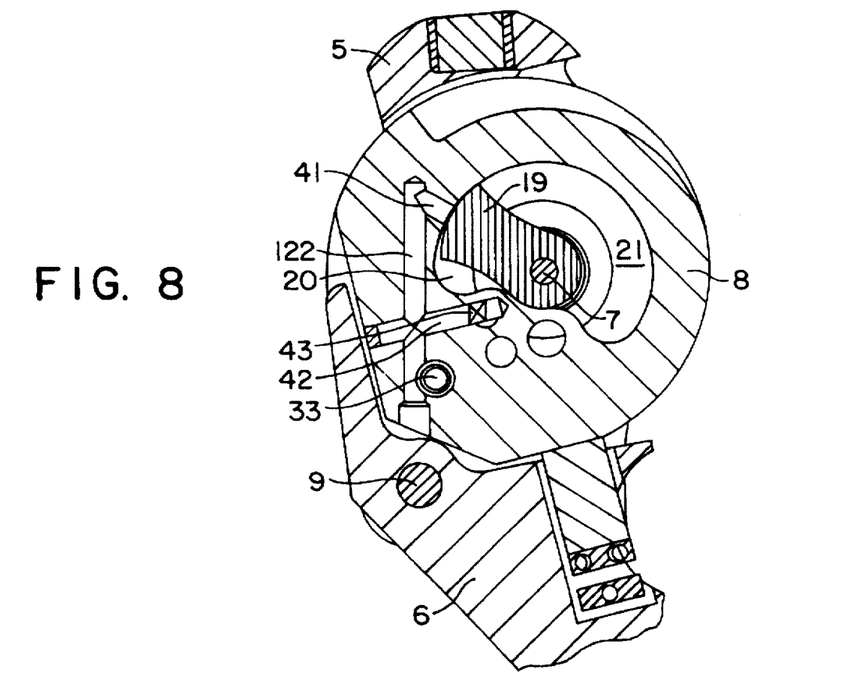
FIG. 8 shows a modified embodiment in a view corresponding to FIG. 4.
Figure 9:
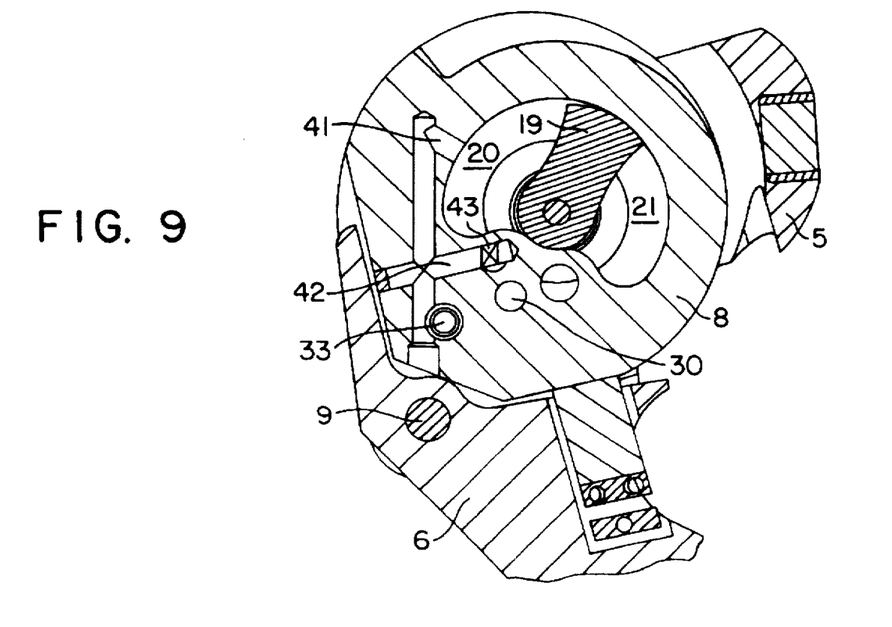
FIG. 9 shows the brake-action knee joint of FIG. 8 in the position of flexion.

In the embodiment shown in FIGS. 8 and 9, end-position damping in the case of extension is provided. The oil line 122 which connects the extension chamber 20 to the flexion chamber 21 is connected in such a way, via a connection 41, to the extension chamber 20 that the rotary piston 19 closes this connection 41 to an increasing extent in the last part of its rotary motion—carried out in the counterclockwise direction—in the direction of extension. This generates a restricting action which effects the damping of extension. The progress of damping here depends on the external shape of the rotary piston 19 moved past the connection 41. A check valve 43 which is opened upon introduction of the bend by the oil displaced from the flexion chamber 21 is inserted into the connection 42 of the oil line 122 to the flexion chamber 21.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

We claim:

1. A brake-action knee joint for a leg prosthesis, comprising:

an upper prosthetic part;

a lower prosthetic part;

a joint pin which includes a rotary piston and which is connected in a torsionally rigid fashion to the upper part of the joint;

a rocker which forms a central part of the joint, the rocker having an extension-side end fixed to a rocker pin lying parallel, ventrally and distally with respect to the joint pin and having a flexion-side end, wherein the rocker surrounds the joint pin; and a braking device activated by foot loading, which includes a closed, fluid-filled displacer chamber;

a valve plunger having an open position and a closed position;

a valve-plunger spring; and a first adjusting device mounted on the lower prosthetic part of the joint and connected to the valve plunger;

wherein the displacer chamber concentrically surrounds the joint pin over its circumference, at least partially and is arranged in an associated end of the central part of the joint, wherein the rotary piston divides the displacer chamber into an extension chamber and a flexion chamber, which are connected to one another by way of an oil line which can be completely or partially closed by the valve plunger;

and wherein the valve plunger is mounted in the central part of the joint in such a way as to be displaceable counter to the action of the valve-plunger spring pushing it into its open position and, when the central part of the joint is pivoted in the direction of flexion about the rocker pin, is pushed into its closed position by the adjusting device.

2. The brake-action knee joint as claimed in claim 1, wherein said first adjusting device is a manually rotatable adjusting screw which acts upon a distal end of the valve plunger.

3. The brake-action knee joint as claimed in claim 1, wherein an extension stop for the prosthetic upper part of the joint is provided on the central part of the joint.

4. The brake-action knee joint as claimed in claim 1, wherein rotary motion of the central part into its position of extension is limited by an extension stop seated on the lower prosthetic part of the joint, and rotary motion of the central part into its position of flexion is limited by a resilient flexion stop likewise fixed to the lower prosthetic part of the joint.

5. The brake-action knee joint as claimed in claim 4, wherein the resilient flexion stop is preloaded by a manually actuable adjusting device.

6. The brake-action knee joint as claimed in claim 5, wherein the first adjusting device is an adjusting screw and wherein the resilient flexion stop includes a rubber sleeve which partially surrounds the valve plunger and the adjusting screw.

7. The brake-action knee joint as claimed in claim 6, wherein the adjusting device for the flexion stop is an adjusting nut which is guided on said adjusting screw and acts upon a distal end of the flexion stop.

8. The brake-action knee joint as claimed in claim 1, wherein a check valve is provided in said oil line, said check valve bypassing a restriction formed by the valve plunger opening upon extension of the joint and the resulting fluid flow from the extension chamber into the flexion chamber.

9. The brake-action knee joint as claimed in claim 8, wherein two oppositely acting restrictor-type check valves are arranged in series in the oil line connecting the extension chamber to the flexion chamber in order to control a swing phase.

10. The brake-action knee joint as claimed in claim 9, wherein, for manual adjustment of a swing-phase control system, the restrictor-type check valves are each acted upon by a respective adjusting pin.

11. The brake-action knee joint as claimed in claim 10, wherein the two restrictor-type check valves have a common ball, which can be displaced between the two adjusting pins.

12. The brake-action knee joint as claimed in claim 11, wherein at least one of the adjusting pins can be displaced in the direction of a valve seat counter to the action of a spring when subjected to sufficient pressure by said ball.

13. The brake-action knee joint as claimed in claim 1, wherein an accumulator which compensates for changes in volume of the fluid, is connected to the displacer chamber.

14. The brake-action knee joint as claimed in claim 1, further comprising a connecting rod which acts as an advancer, one end of which is pivoted to the upper prosthetic part of the joint and the distal end of which is pivoted to a spring clamp which is accommodated in the lower prosthetic part of the joint and is acted upon by an advancer spring.

15. The brake-action knee joint as claimed in claim 1, wherein, to generate end-position damping upon extension, the oil line which connects the extension chamber to the flexion chamber is connected in such a way, via a connection, to the extension chamber that the rotary piston closes this connection to an increasing extent in the last part of its rotary motion in the direction of extension.

16. The brake-action knee joint as claimed in claim 15, wherein a check valve, which is opened upon flexion of the knee joint by the fluid displaced from the flexion chamber, is inserted into the connection of the oil line to the flexion chamber.

* * * * *